(12) United States Patent
Chang et al.

(10) Patent No.: US 8,227,258 B2
(45) Date of Patent: Jul. 24, 2012

(54) DELIVERY AND SENSING OF METERED AMOUNTS OF LIQUID MATERIALS

(75) Inventors: Timothy N. Chang, Montville, NJ (US); Qiong Shen, Kearny, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 531 days.

(21) Appl. No.: 12/369,295

(22) Filed: Feb. 11, 2009

(65) Prior Publication Data

US 2009/0253216 A1 Oct. 8, 2009

Related U.S. Application Data

(60) Provisional application No. 61/065,362, filed on Feb. 11, 2008.

(51) Int. Cl.
*G01N 1/10* (2006.01)
*G01N 21/00* (2006.01)

(52) U.S. Cl. ........ 436/180; 436/164; 436/165; 436/169; 436/170; 422/119; 422/416; 422/430; 422/400; 422/401; 422/420; 422/421; 422/422; 422/423; 422/424; 422/425; 422/426; 422/427; 422/428; 422/429; 422/501; 422/503; 422/515; 422/519; 422/521; 422/553; 422/68.1; 422/82.05; 422/82.06; 435/13; 435/283.1; 435/287.1; 435/287.7; 435/287.8; 435/287.9; 435/288.7; 141/1; 141/101; 141/283; 73/1.36; 73/1.73; 73/1.74; 73/649; 73/655; 73/656; 73/864.01; 73/864.13; 73/864.24; 700/282; 700/283

(58) Field of Classification Search ............... 422/82.05, 422/501, 519, 515, 521, 119, 416, 430, 400, 422/401, 420, 421, 422, 423, 424, 425, 426, 422/427, 428, 429, 503, 553, 68.1, 82.06; 436/180, 164, 165, 169, 170; 435/13, 283.1, 435/287.1, 287.7, 287.8, 287.9, 288.7; 141/1, 141/101, 283; 73/1.36, 1.73, 1.74, 649, 655, 73/656, 864.01, 864.13, 864.24; 700/282, 700/283

See application file for complete search history.

(56) References Cited

U.S. PATENT DOCUMENTS 4,378,493 A 3/1983 Dorf et al.
(Continued)

OTHER PUBLICATIONS

Zuech, "Update on Machine Vision-Based Web Scanners for Sheet Production Inspection," available at http://www.machinevisiononline.org/public/articles/details.cfm?id=1281, printed on Jan. 12, 2010 (10 pages).
(Continued)

*Primary Examiner* — Dennis M White
(74) *Attorney, Agent, or Firm* — McCarter & English, LLP

(57) ABSTRACT

A liquid delivery apparatus is provided for depositing liquid materials onto prescribed areas. The apparatus includes a sensing and delivery pin and a photo sensor. The apparatus is sized to deliver a droplet of liquid material to the surface of a target area without coming into contact with the target surface. The apparatus is also capable of drawing geometric features, such as lines and grids of liquid material. The photo sensor measures the intensity of light during a processing cycle. Measured reflected-light intensity can be compared in real-time to a reference curve which is based on test process cycles representing the light intensity expected when the process proceeds in the preferred fashion to produce a normal spot having an expected droplet size. The light intensity measurements can also be fitted with a mathematical function such as an asymmetric double sigmoidal curve.

9 Claims, 12 Drawing Sheets

U.S. PATENT DOCUMENTS

| | | | |
|---|---|---|---|
| 4,750,131 | A | 6/1988 | Martinez |
| 4,855,923 | A | 8/1989 | Fullmer |
| 4,987,528 | A | 1/1991 | O'Brien |
| 5,586,041 | A | 12/1996 | Mangrulkar |
| 7,097,810 | B2 | 8/2006 | Chang et al. |
| 2004/0026007 | A1 * | 2/2004 | Hubert et al. .......... 156/64 |
| 2004/0179972 | A1 | 9/2004 | Karp et al. |
| 2006/0240566 | A1 | 10/2006 | Chang et al. |

OTHER PUBLICATIONS eFunda: Introduction to Fiber Optic Sensors, available at http://www.efunda.com/DesignStandards/sensors/fotonic/fontonic_intro.cfm (2007) (4 pages).

eFunda: Theory of Fiber Optic Sensors, available at http://www.efunda.com/designstandards/sensors/fotonic/fontonic_theory.cfm (2007) (3 pages).

Dierker, et al., "Process Signature Verification for Device Manufacturing," Medical Device & Diagnostic Industry, Sep. 2005 (6 pages).

McMahon, "Signature Analysis System: New Technology to Enhance Quality in Manufacturing," Sensor Review, vol. 20, No. 2, 2000 (8 pages).

Shen, et al., "Automated Real-Time Spotting System for DNA/Protein Microarray Applications," IEEE, 2007 (6 pages).

Shen, et al., "SmartPin—An Automated Multi-Function Liquid Dispensing System," The 33rd Annual Conference of the IEEE Industrial Electronics Society, Nov. 5-8, 2007 (6 pages).

Chang, et al., "Automated Liquid Dispensing Pin for DNA Microarray Applications," IEEE Transactions on Automation Science and Engineering, vol. 3, No. 2, Apr. 2006 (5 pages).

\* cited by examiner

DELIVERY AND SENSING OF METERED AMOUNTS OF LIQUID MATERIALS

CROSS-REFERENCE TO RELATED APPLICATION

This application claims the benefit of U.S. Provisional Patent Application No. 61/065,362 filed Feb. 11, 2008, the disclosure of which is incorporated herein by reference in its entirety.

FIELD OF THE INVENTION

The present invention relates to delivery of metered amounts of liquid materials, and determining the sufficiency of the delivered material.

BACKGROUND OF THE INVENTION

Liquid dispensing systems capable of drawing patterned microlines for use in applications, such as in organic electronics, use various approaches. Such approaches include microcontact printing, screen-printing, photolithographic printing, and inkjet printing. These systems place small amounts of liquid containing semiconducting polymer molecules or conducting ink particles onto a substrate to form circuitry. It is important that the dispensed liquid be of a generally sufficient quantity for proper subsequent process. None of the prior approaches, however, includes an intrinsic mechanism to sense the properties of the dispensed liquid. While exterior vision systems have been employed to sense the liquid dispensing process, it would be difficult to detect defective spots in a practical and accurate manner using these systems. In addition, these exterior vision systems increase the cost of the overall system.

In addition, none of these approaches lends themselves to the detection, in real-time, of defective deposition patterns. Thus, it would be desirable to develop an improved noncontact liquid dispensing system which allows for the detection of defects in-situ and in real-time.

SUMMARY OF THE INVENTION

A liquid delivery apparatus is provided for depositing liquid materials onto prescribed areas, such as target areas on a microarray. The liquid delivery apparatus includes a sensing and delivery pin and a pin actuator for vertically driving the pin relative to a housing. The liquid delivery apparatus also includes a photo sensor, a cavity, and a plunger configured to aspire liquid material into the cavity.

The liquid delivery apparatus is sized to deliver a droplet of liquid material contained in the cavity to the surface of a target area without coming into contact with the target surface. The liquid delivery apparatus is also capable of drawing geometric features, such as lines and grids of liquid material, which is useful in various applications such as biological arrays and semiconductor systems.

The photo sensor includes a light source, a beam splitter or a coupler, and photodetectors. The splitter is sized to send a portion of the light from the light source to the photodetector which monitors the intensity of the source, and is sized to send a portion of the light from the light source through the pin and onto the target surface. Alternatively, a light coupler may be used. The photo sensor is provided for sensing and measuring the light reflected from the target surface and transmitted through the pin. The intensity of the reflected light measured by the photodetector provides an indication of the size of the dispensed liquid material and the presence/absence of a defective droplet in real-time.

Measured reflected-light intensity can be compared to a reference curve which is based on test process cycles representing the light intensity expected when the process proceeds in the preferred fashion to produce a normal spot having an expected droplet size. The profile of the actual light intensity received during the operation of the process can be compared in real-time against the profile of the reference curve. Significant variations between the profile of the real-time measurements and the profile of the reference curve indicate that a defective deposition pattern was created. The light intensity measurements can also be fitted with a mathematical function such as an asymmetric double sigmoidal curve.

A method is disclosed for dispensing a liquid material. The liquid delivery apparatus, having liquid material contained in a cavity, is moved toward a predetermined location until a droplet of liquid material formed on a tip of the liquid delivery apparatus contacts the predetermined location. The intensity of light is measured during this step, and this step is monitored in real-time based on the measured light intensity. The liquid delivery apparatus can be moved horizontally along a predetermined area after the liquid material elongates, while the liquid material is continuously dispensed, to generate a line of liquid material.

The liquid delivery system includes the liquid delivery apparatus, which includes a cavity sized to contain liquid material, and the pin. The system also includes a positioning stage adapted to move the liquid delivery apparatus toward a predetermined location until a droplet of liquid material formed on a tip of the liquid delivery apparatus contacts the predetermined location. A light sensor is provided to measure the intensity of light transmitted through the pin.

BRIEF DESCRIPTION OF THE DRAWINGS

For a more complete understanding of the present invention, reference is made to the following Detailed Description of the Invention, considered in conjunction with the accompanying drawings, in which.

DETAILED DESCRIPTION OF THE INVENTION

Figure 1:
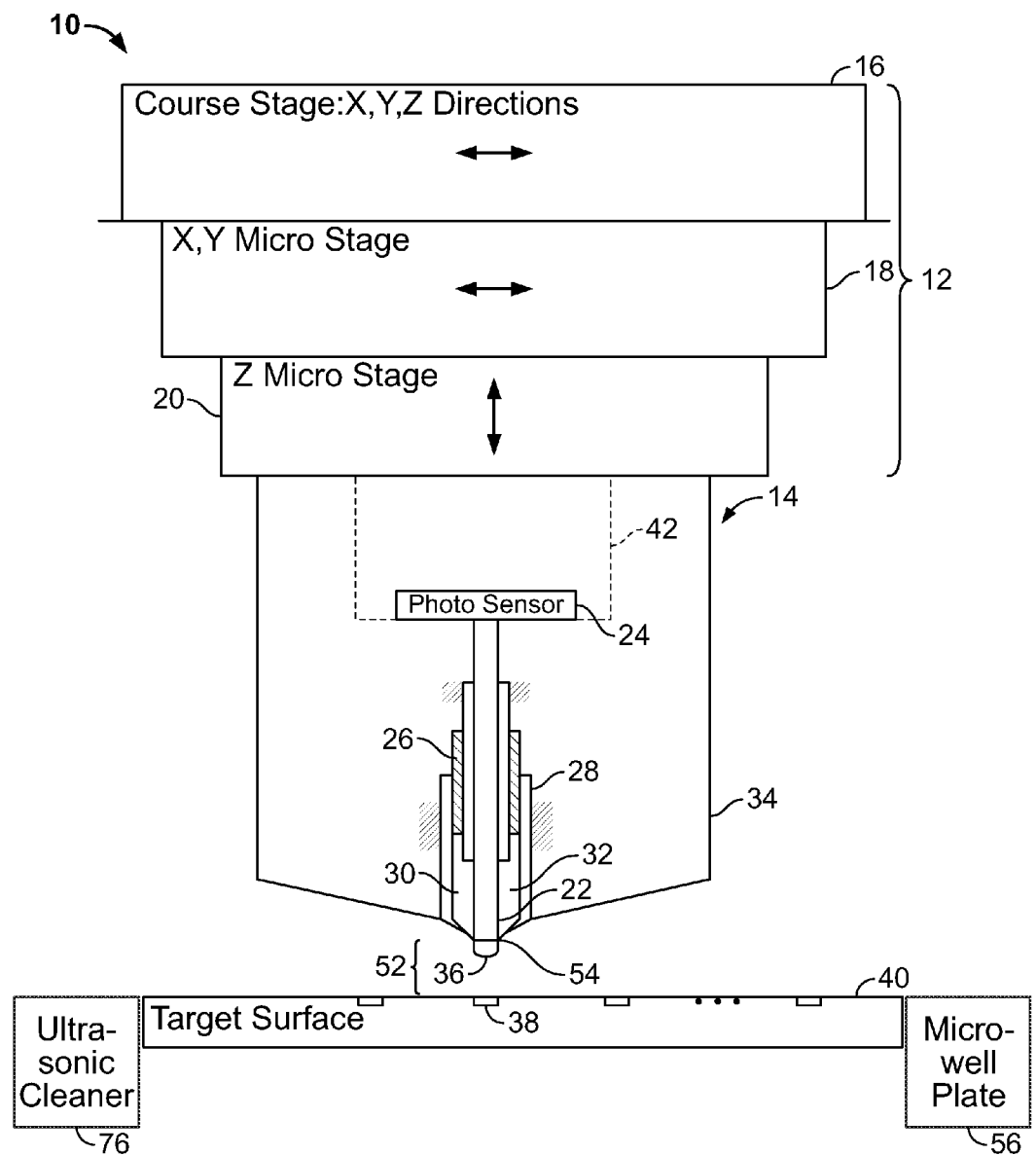
FIG. 1 is a cross-section diagram of a liquid delivery system.

FIG. 1 illustrates a liquid delivery system 10 that includes a positioning stage 12 and a liquid delivery apparatus 14 connected to the positioning stage 12. The positioning stage 12 includes a coarse positioning stage 16, a horizontal axis microstage 18, and a vertical axis microstage 20. Coarse positioning can be accomplished using robotic techniques having a wide range of motion. The microstages 18, 20 serve to finely position the liquid delivery apparatus 14. More particularly, the horizontal microstage 18 provides fine positioning in the X, Y directions, whereas the vertical microstage 20 provides fine positioning in the Z direction, as described in U.S. Pat. No. 7,097,810 B2. The disclosure of U.S. Pat. No. 7,097,810 B2 is incorporated herein by reference in its entirety.

With reference to FIG. 1, the liquid delivery apparatus 14 is provided for depositing liquid materials onto preselected areas. The liquid delivery apparatus 14 can deliver liquid sample materials including nucleic acids, proteins, polypeptides, or other materials to precise areas such as the target areas on a microarray. Liquid materials include, for example, pure liquid compounds, mixtures, solutions, emulsions or dispersions. The liquid buffer material can be clear or light transparent so light can transmit therethrough. Examples of liquid buffer materials include water, ethanol or glycerol.

The liquid delivery apparatus 14 generally includes a sensing and delivery pin 22, a photo sensor 24, a plunger 26, a cylindrical hollow tubing such as a pulled capillary glass tube 28, and a cavity 30 sized to contain liquid material 32, each of which is contained in a housing 34. As will be explained in further detail hereinafter, the liquid delivery apparatus 14 is sized to deliver a droplet, such as the liquid bulge 36 (see FIG. 1), of the liquid material 32 contained within the cavity 30 to a target area 38 on a target surface 40 without coming into contact with the target surface 40. A pin actuator 42 is provided for vertically driving the pin 22 relative to the hollow tubing and the housing 34. The pin 22 can be made from a segment of optical fiber, as described in U.S. Pat. No. 7,097,810 B2.

Figure 2:
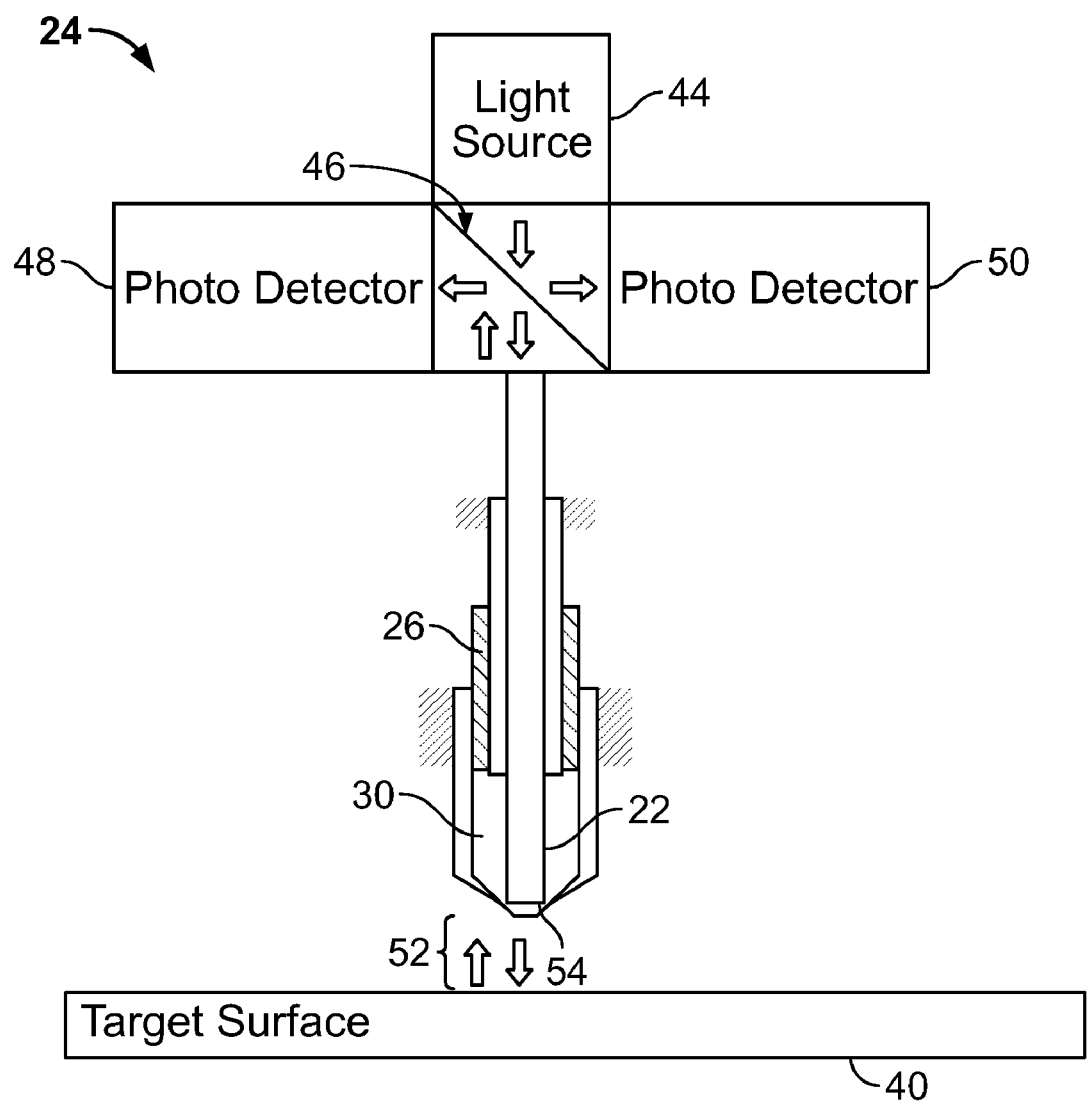
FIG. 2 is a diagram of a photo sensor used in the liquid delivery system.

Referring to FIG. 2, the photo sensor 24 is used to sense the light reflected from the target surface 40 and transmitted through the pin 22. The sensor 24 is connected to a top portion of the pin 22 and is vertically translatable with the pin 22. As described in further detail in U.S. Pat. No. 7,097,810 B2, the photo sensor 24 includes a light source 44, a beam splitter 46, and photodetectors 48, 50. The splitter 46 is sized to send a portion of the light from the light source 44 to the photodetector 48 which monitors the intensity of the source, and is sized to send a portion of the light from the light source 44 through the pin 22 and onto the target surface 40. The splitter 46 also sends reflected light passing back up through the pin 22 to the photodetector 50, which monitors the intensity of the reflected light. Alternatively, a photo coupler may be used in lieu of the beam splitter. The distance 52 between the tip 54 of the liquid delivery apparatus 14 and the target surface 40 can be determined based on the reflected light. Alternatively, optical transmission can be one-way as described in U.S. Pat. No. 7,097,810 B2. The photo sensor could be an optical lever based proximity sensor such as the Fotonic™ Sensor manufactured by MTI Instruments, Inc., based in New York.

Liquid material is aspirated into the cavity 30 during a preparation step. More particularly, the liquid delivery apparatus 14 is moved toward the location of liquid materials, such as a micro-well plate 56, via the positioning stage 12. After dipping into the specified liquid material, the plunger 26 is pulled upwards to aspire the liquid material into the cavity 30. The cavity 30 could be sized such that from tens of nanoliters to a few microliters of liquid material or more can be aspirated for a pin with a sixty micron diameter. Because liquid residue is undesirably formed on the exterior sidewall of the tip 54 of the liquid delivery apparatus 14 during aspiration, pre-spotting on a specified preparation area is performed until this residue is removed.

Figure 3:
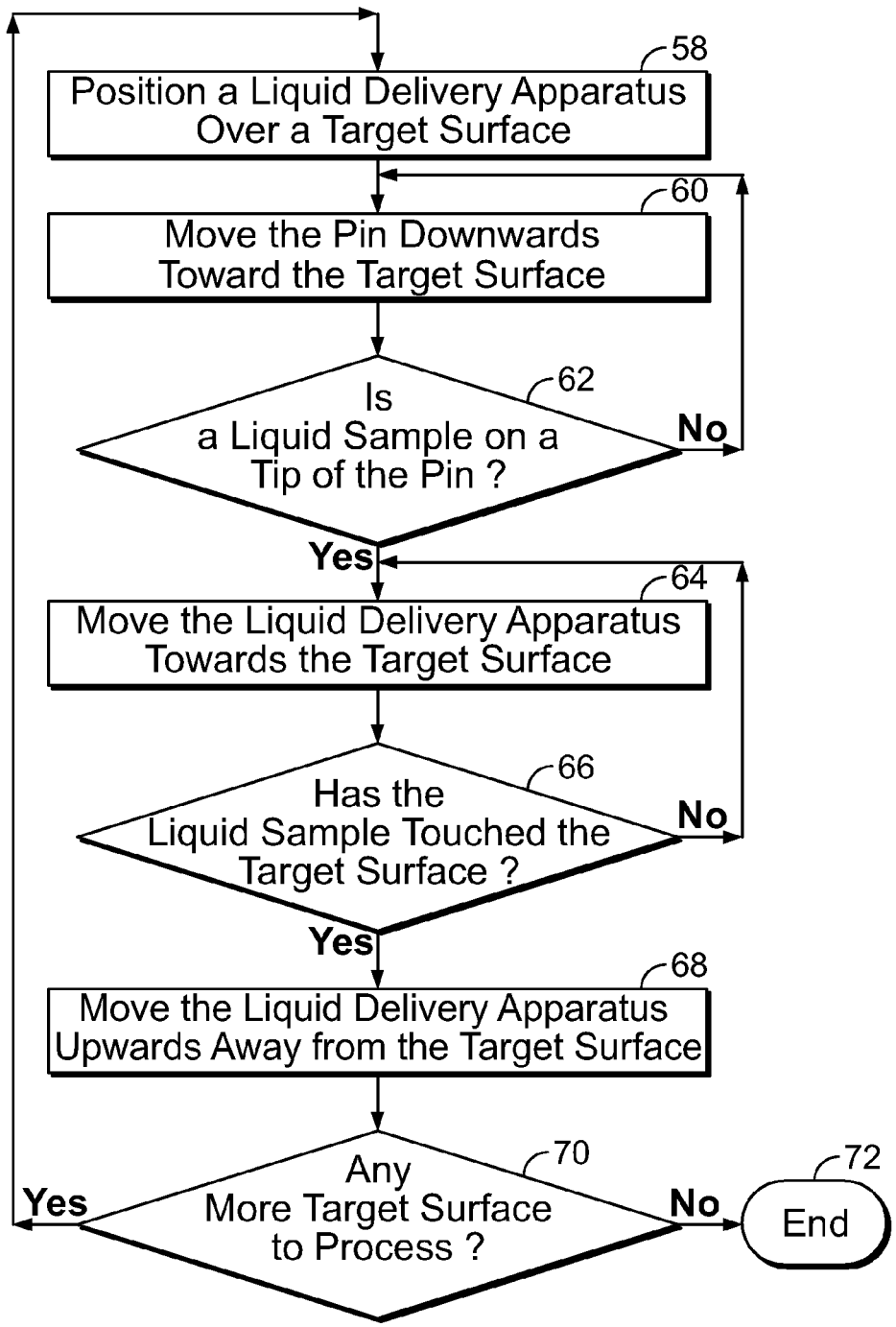
FIG. 3 is a flow chart of the operation of the liquid delivery system.

FIG. 3 is a flow diagram illustrating the operation of a typical process cycle used to deposit a droplet, such as the liquid bulge 36, on a target area, such as the target area 38 of the target surface 40. The typical process cycle includes several steps and four distinct phases as will be described in further detail hereinafter.

Figure 4A:
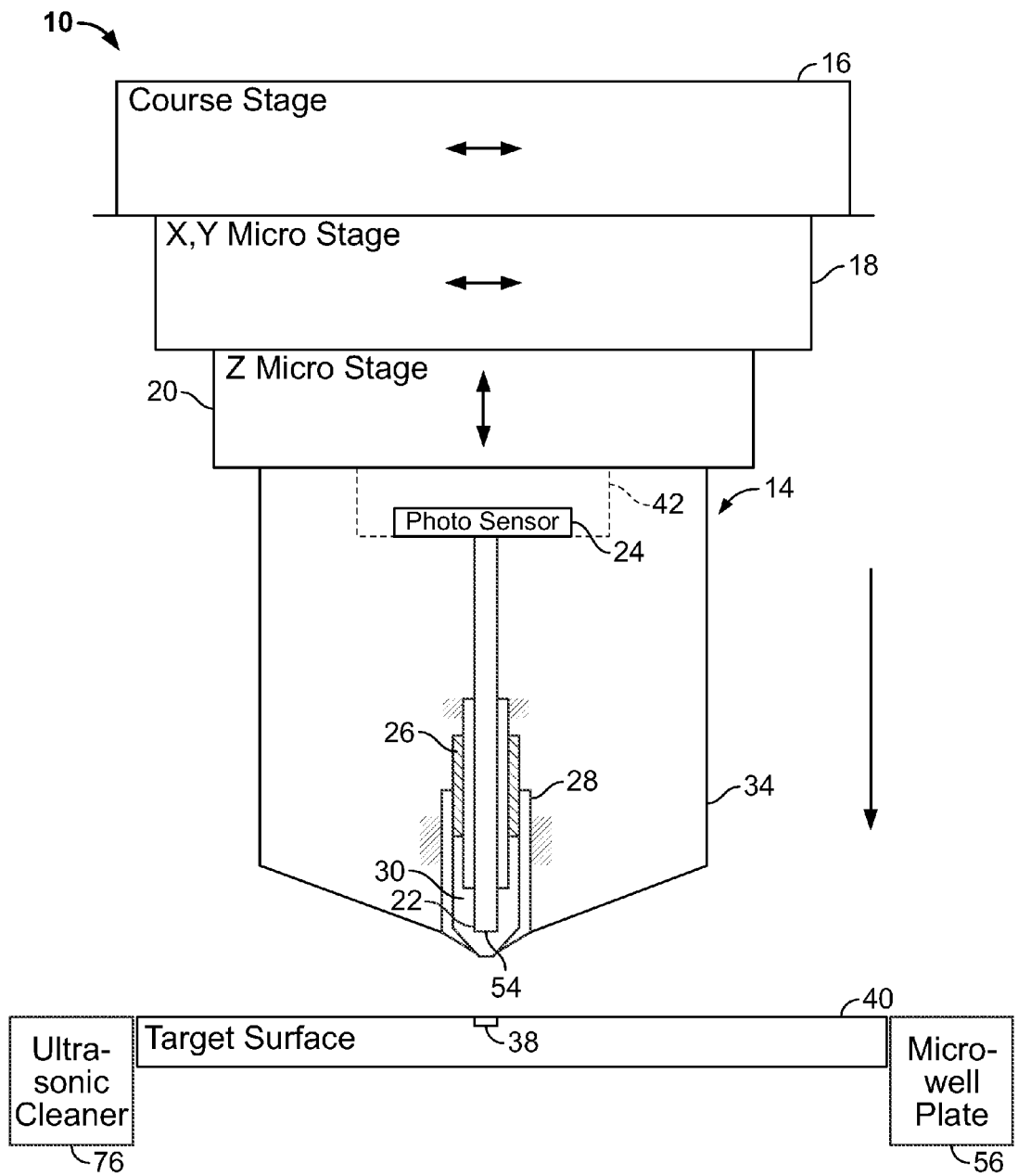
FIGS. 4A-4E illustrate the operation of the liquid delivery system during different stages.
Figure 4B:
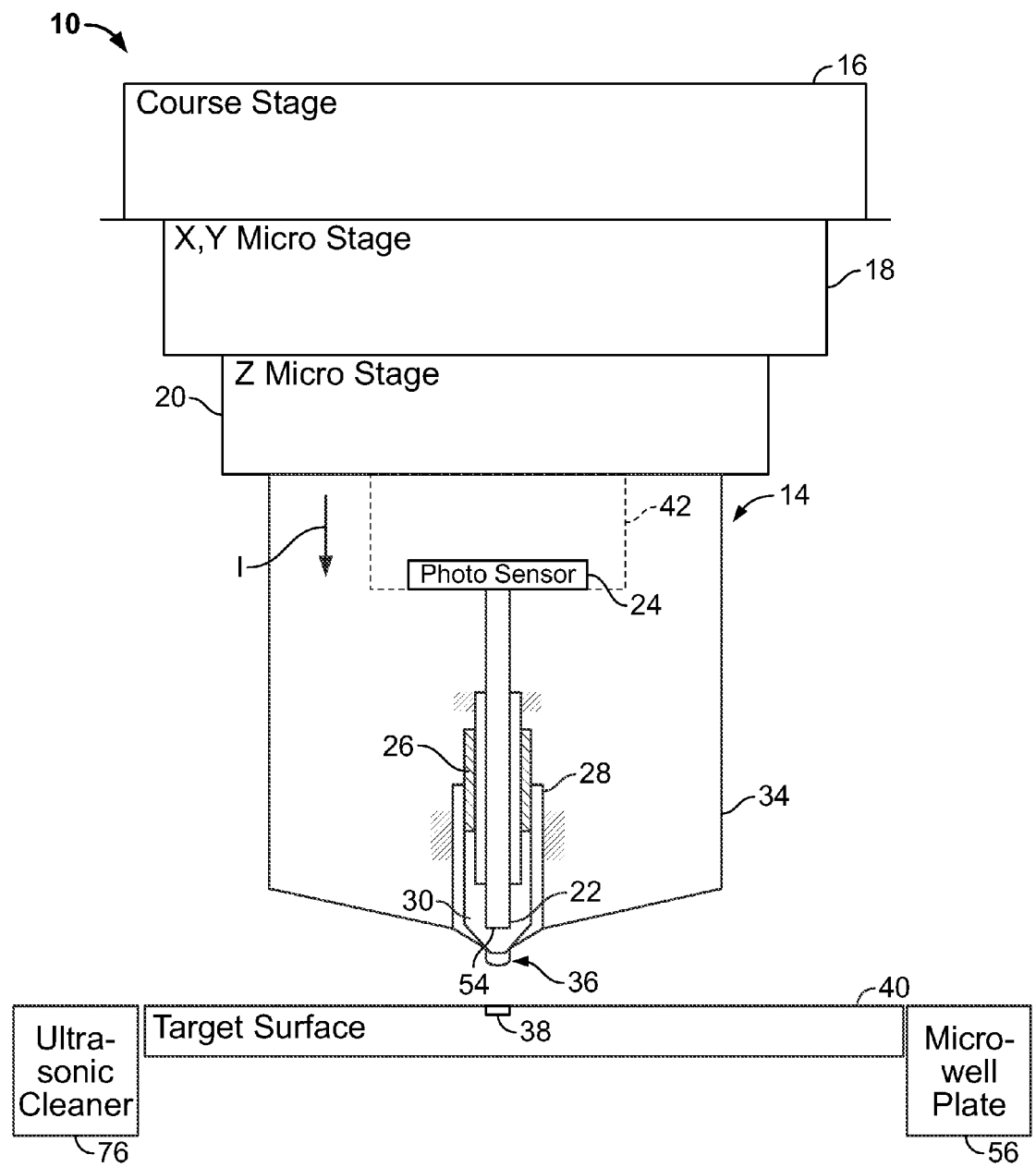

With reference to FIG. 4A, after liquid material is aspired into the cavity 30, the process begins at step 58 wherein the liquid delivery apparatus 14 is moved toward the target area 38 of the target surface 40 via the positioning stage 12. In the next step 60, which is illustrated in FIG. 4B, once the liquid delivery apparatus 14 is positioned over the target surface 40, the pin 22 approaches and moves downward toward the target area 38 of the target surface 40, whereby a predetermined amount of the liquid material 32 is carried from the cavity 30 to form the liquid bulge 36. Alternatively, the plunger 26 could move downward toward the target area 38 of the target surface 40 to push a predetermined amount of the liquid material 32 from the cavity 30. The liquid bulge 36 remains on the surface of the tip 54 of the liquid delivery apparatus 14 as a result of forces such as surface tension or capillary action.

In step 62, a determination is made as to whether the liquid bulge 36 is adhered to the tip 54 of the liquid delivery apparatus 14. This determination is made by comparing the light intensity that is expected at this time with the received light intensity, as described in U.S. Pat. No. 7,097,810 B2. If there is no match between the expected light intensity and the received light intensity, the process returns to step 60 where the pin 22 is moved further downward toward the target surface 40 until the liquid bulge 36 is attached to the tip 54 of the liquid delivery apparatus 14 and there is a substantial match between the received and the expected light intensity values. Alternatively, with the pin 22 fixed inside the cavity 30, the plunger 26 is actuated toward the target surface to expel a metered amount of liquid to form the bulge 36.

Figure 4C:
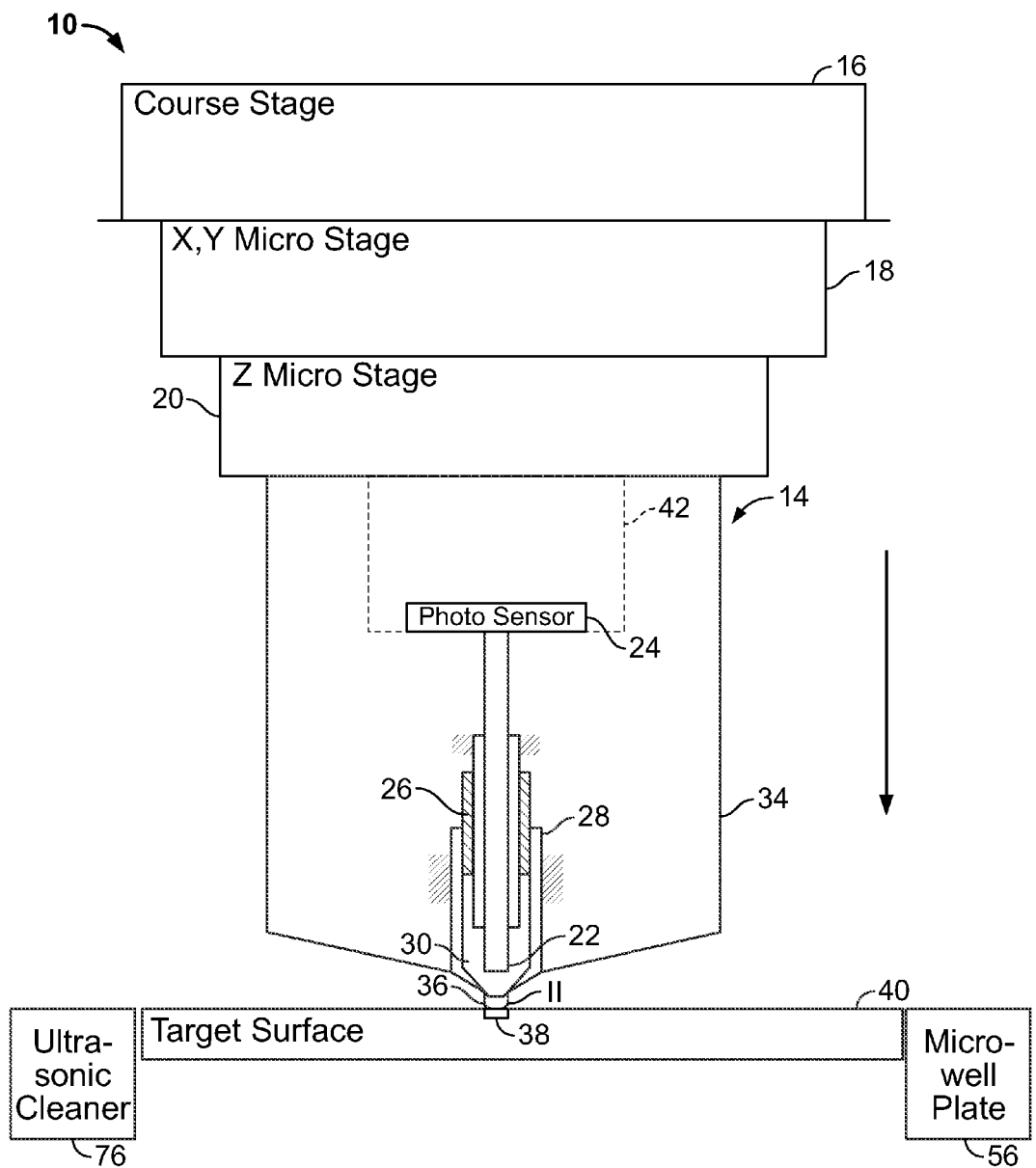

Referring to FIG. 4C and step 64, the liquid delivery apparatus 14 further approaches and moves downward toward the target area 38 of the target surface 40 until the liquid bulge 36 touches the target area 38. The target surface 40, which is typically glass, could be coated with a hydrophilic material which bonds the liquid bulge 36 to the target surface 40 as soon as the liquid bulge 36 touches the target surface 40. Because the liquid bulge 36 touches the target area 38, the liquid delivery system 10 can be used to generate lines of liquid material, as will be described in further detail hereinafter.

In step 66, a determination is made as to whether the liquid bulge 36 has touched the target area 38. This determination is made by comparing the light intensity that is expected at this time with the received light intensity. This expected value represents the light intensity as a result of the liquid bulge 36 touching the target area 38. If there is no match between the expected light intensity and the received light intensity, the process returns to step 64 where the liquid delivery apparatus 14 is moved further downward toward the target area 38 until the liquid bulge 36 touches the target area 38.

As indicated above, the typical process cycle includes four distinct phases. In the first phase I, the light intensity increases as the liquid delivery apparatus 14 approaches and moves downward toward the target area 38 of the target surface 40 (see FIGS. 4B and 4C). In the second phase II, when the liquid bulge 36 touches the target area 38 (see FIG. 4C), most of the light energy is transmitted through the liquid bulge 36 into the target area 38, which causes a large drop in reflected light intensity.

Figure 4D:
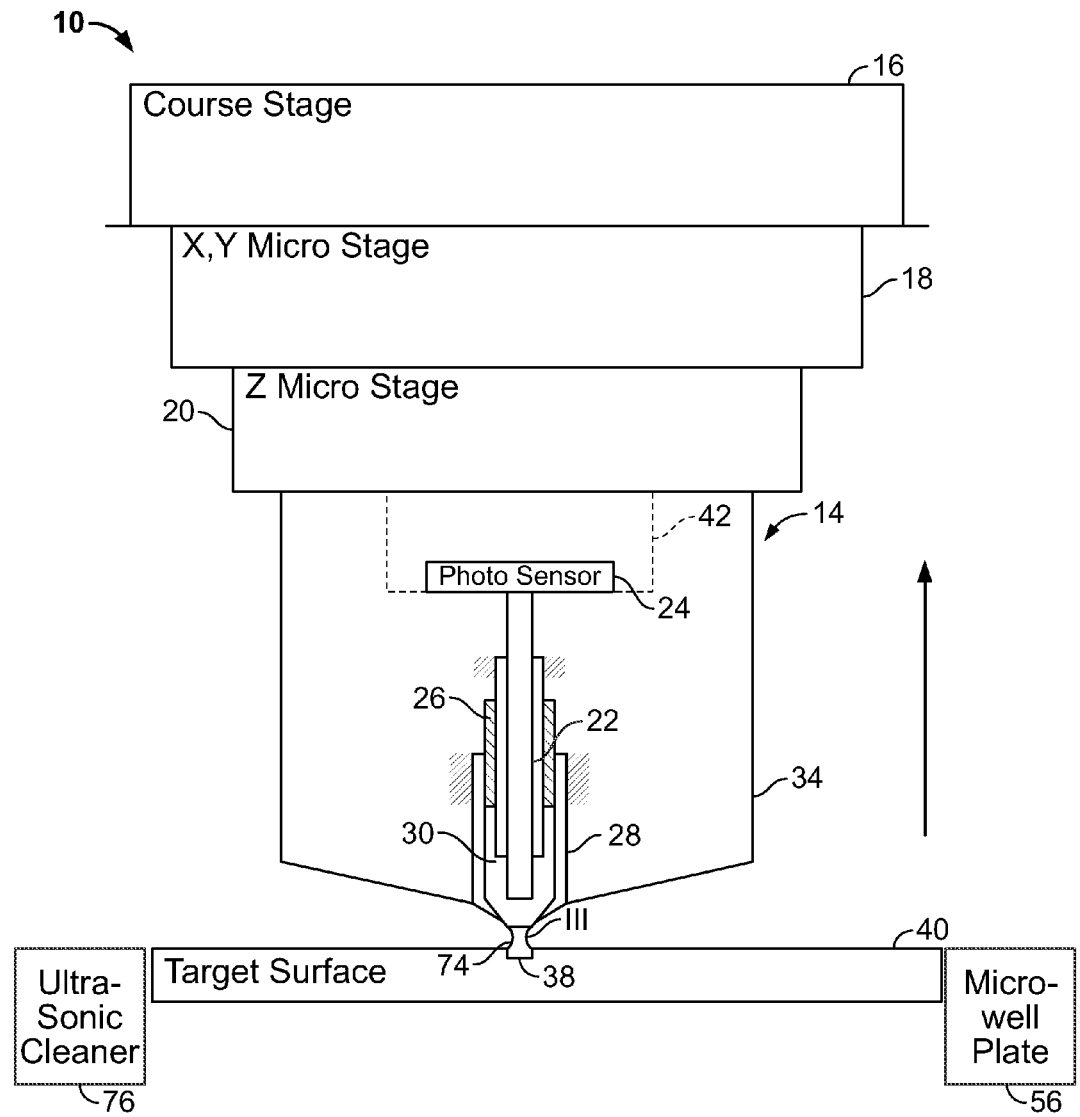
Figure 4E:
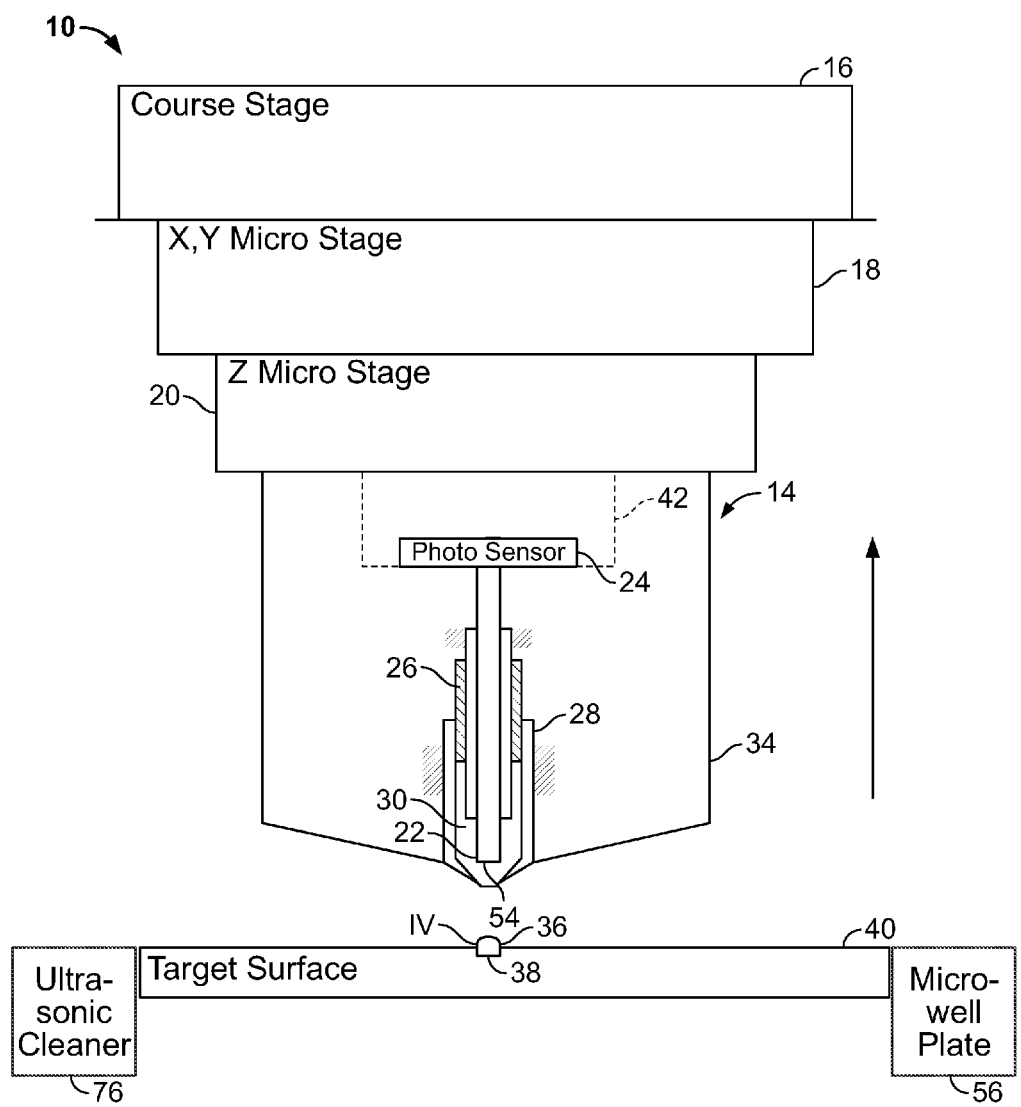

Referring to FIG. 4D and step 68, once the liquid bulge 36 touches the target area 38, the liquid delivery apparatus 14 moves in the upward direction away from the target surface 40. In the third phase III, as the liquid delivery apparatus 14 is being moved in the upward direction away from the target surface 40, the liquid bulge 36 elongates and forms a liquid column 74, as shown in FIG. 4D. The formation of the liquid column 74 permits light transmission from the sensor to the target area and hence causes the light intensity to remain at a low level. As the liquid delivery apparatus 14 continues to move in the upward direction away from the target surface 40, the liquid column 74 pinches off, as shown in FIG. 4E. In the fourth phase IV, when the liquid column 74 pinches off, the reflected light intensity increases. This is because the index of refraction of air is lower than that of the liquid and hence total internal reflection takes place.

In step 70, a determination is made as to whether each of the target areas 38 has been processed as the liquid delivery apparatus 14 is being moved in the upward direction away from the target surface 40. If each of the target areas 38 has been processed, the process cycle for a target surface 40 is complete (step 72) and the processed target surface can be removed and replaced with a new target surface for the next process cycle. At the end of processing for each type of liquid material, the liquid delivery apparatus 14 is moved toward an ultrasonic cleaner 76. The liquid delivery apparatus 14 is dipped into the ultrasonic cleaner 76 with the repeated up/down movements of the pin 22 or the plunger 26 to clean the inner and outer areas of the glass tube 28. A water bath (not shown) can be used rather than the ultrasonic cleaner 76.

Figure 5:
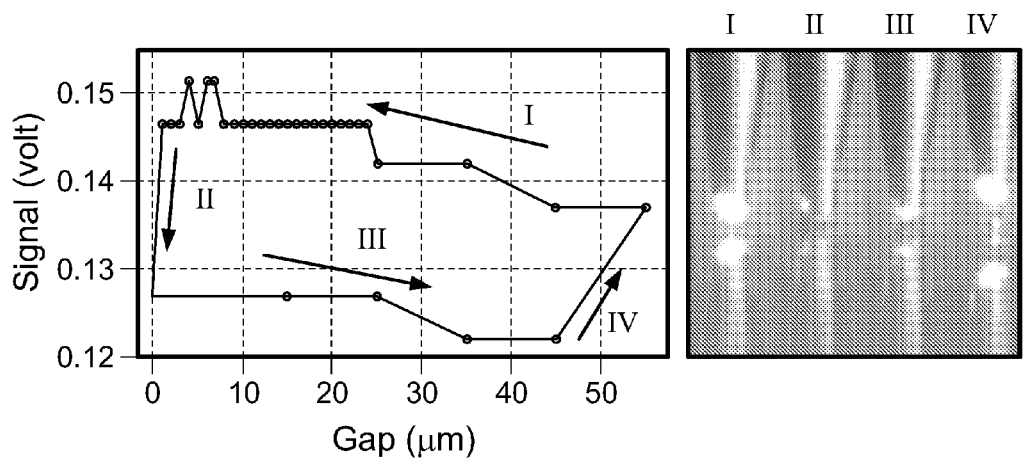
FIG. 5 is a graph comparing light intensity to the gap (distance) between the tip of the liquid delivery apparatus and the target surface during the execution of a typical process cycle.

FIG. 5 is a graphical illustration of the four distinct phases used to form an expected droplet size. The graphical illustration compares the light intensity to the gap (distance) between the tip 54 of the liquid delivery apparatus 14 and the target surface 40 during the execution of a typical process cycle. The light intensity values are provided in magnitude units, such as volts, representing the intensity of light received at the photo sensor 24. The gap values are provided in length units, such as micrometers.

Figure 6:
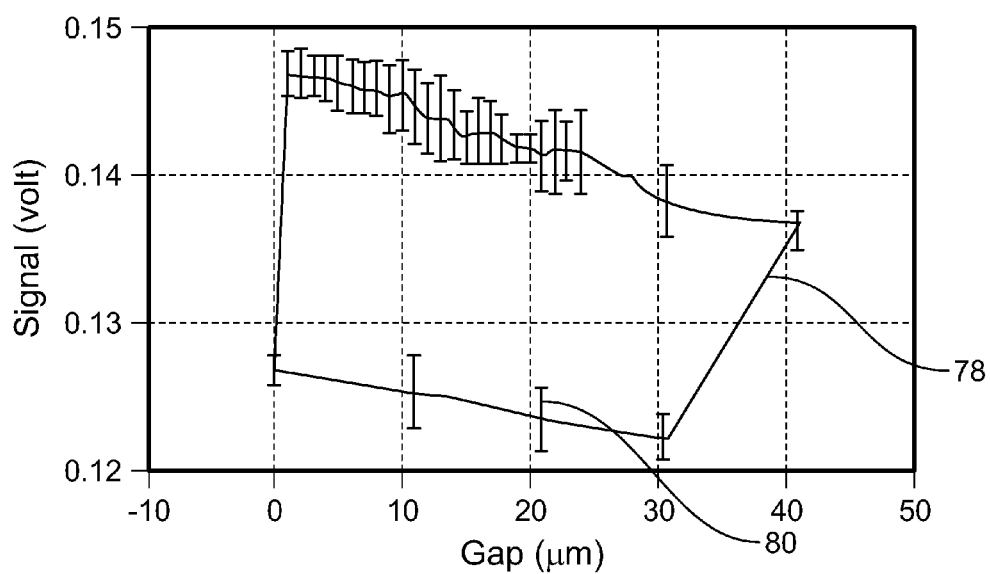
FIG. 6 is a graph of the profile of the light intensity received during the execution of a typical process cycle that produces an expected droplet size.

Test process cycles are executed to determine the average light intensity for each phase. The data produced during the test process cycles is used to derive a profile for a reference (empirical) curve 78 (see FIG. 6) representing the light intensity expected when the process proceeds in the preferred fashion to produce a normal spot having an expected droplet size. This data can be averaged to generate the reference curve 78 shown in FIG. 6 with one sigma error bar 80. The error bars 80 shown in FIG. 6 indicate that the expected droplet size falls within a predetermined range of variations.

The profile of the actual light intensity received during the operation of the process can be compared in real-time against the profile of the reference curve 78. Significant variations between the profile of the real time measurements and the profile of the reference curve 78 indicate that a defective spot was created. For example, a significant variation could indicate that the spot is abnormally big, misshaped, or missing/extremely dim. Pre-set tolerances can be used to determine whether a variation between the profile of the real-time measurements and the profile of the reference curve 78 is significant. A spot could be considered abnormally big, for example, if its area is bigger than double the median spot area. A spot could be considered misshaped, for example, if its scanned center location deviates from the predefined center location more than ⅛ of the spot diameter. A spot could be considered missing, for example, if the total intensity of the spot is lower than 1/10 of the median total intensity. Examples of profiles of defective spots are provided below.

Figure 7:
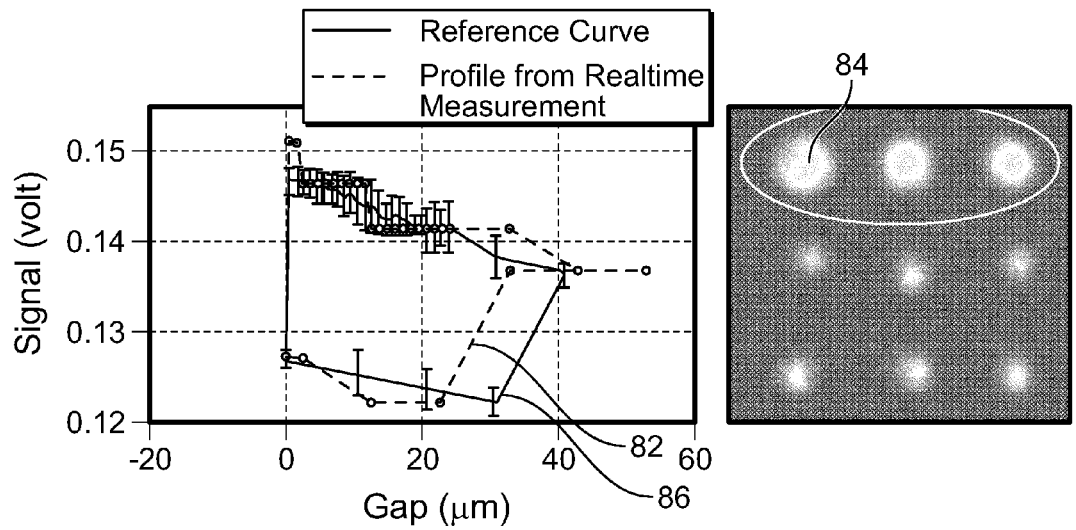
FIG. 7 is a graph comparing the profile of the actual light intensity received during the operation of a process that produces an abnormally big spot to the profile of the reference curve.

FIG. 7 is a graph comparing the profile 82 of the actual light intensity received during the operation of a process that produces an abnormally big spot 84 to the profile 86 of the reference curve 78. With reference to FIG. 7, the profile 82 of the abnormally big spot 84 has a higher first phase I signal level, a larger high peak signal value, a lower third phase III intensity, and a shorter third phase III relative to the reference curve 78.

Figure 8:
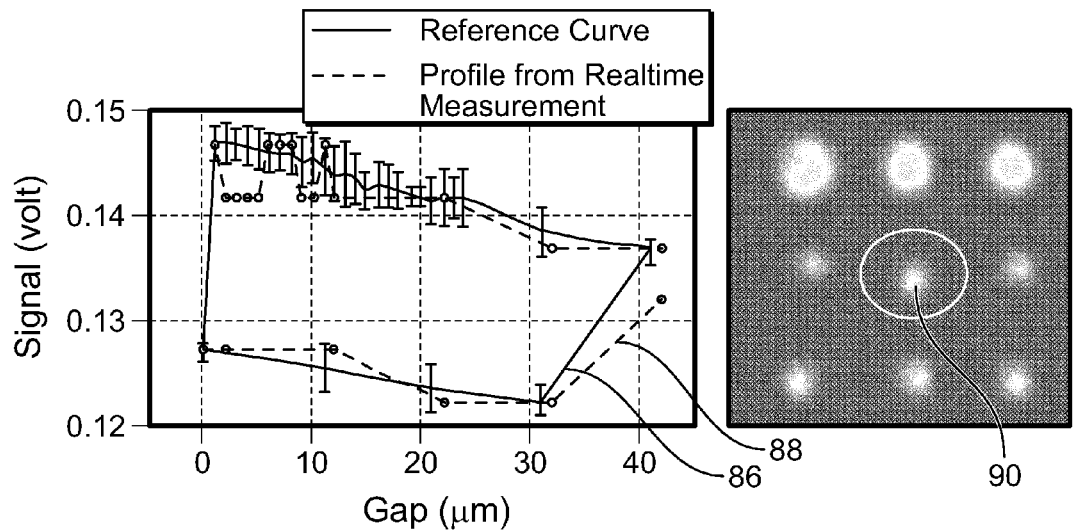
FIG. 8 is a graph comparing the profile of the actual light intensity received during the operation of a process that produces a misshaped spot to the profile of the reference curve.

FIG. 8 is a graph comparing the profile 88 of the actual light intensity received during the operation of a process that produces a misshaped spot 90 to the profile 86 of the reference curve 78. With reference to FIG. 8, the profile 88 of the misshaped spot 90 includes an incomplete curve at the end of the fourth phase IV.

Figure 9:
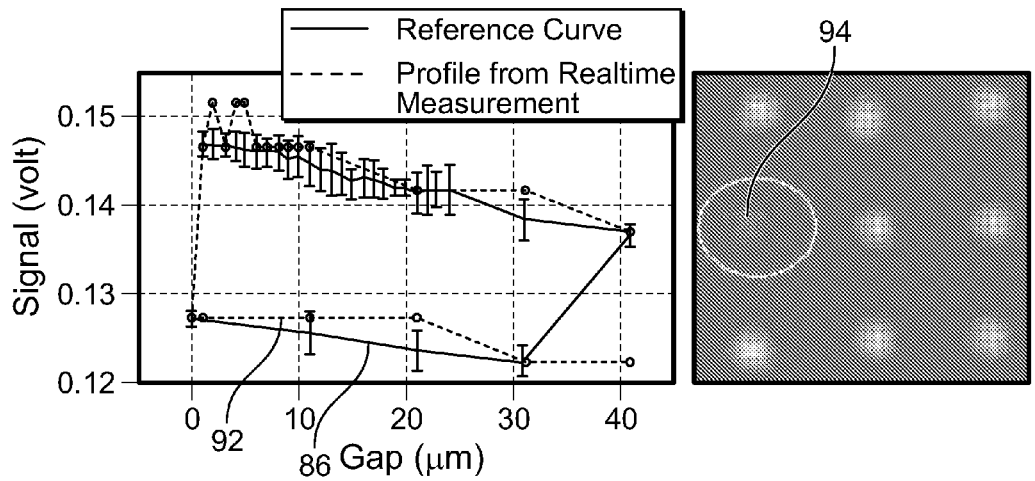
FIG. 9 is a graph comparing the profile of the actual light intensity received during the operation of a process that produces a missing/extremely dim spot to the profile of the reference curve.

FIG. 9 is a graph comparing the profile 92 of the actual light intensity received during the operation of a process that produces a missing spot 94 to the profile 86 of the reference curve 78. With reference to FIG. 9, the profile of the missing spot 94 includes a larger high peak signal intensity, higher second phase II signal intensities, and a delayed fourth phase IV relative to the reference curve 78.

The light intensity measured by the photo sensor 24 can provide an indication of the size of the dispensed liquid material and the presence/absence of the droplet in real-time, as the droplet is being dispensed onto a substrate. Thus, the present invention provides a non-contact optical method for real-time measurement of light intensity to detect defects, thereby eliminating the need to monitor the operation of the liquid delivery system 10 from a separate apparatus, such as a vision system involving video cameras.

In addition to the method of comparing real time and stored light intensities described above, the light intensity measured by the photo sensor 24 can also be fitted using a mathematical function such as an asymmetric double sigmoidal (ADS) curve which has six coefficients and can fit the light intensity versus time during phases I-IV during dispensation of a spot. A typical ADS function with six coefficients is given below:

$$y = a + \left(\frac{b}{1+e^{\frac{-(x-c+d/2)}{e}}}\right)\left(1 - \frac{1}{1+e^{\frac{-(x-c-d/2)}{f}}}\right)$$

Figure 10:
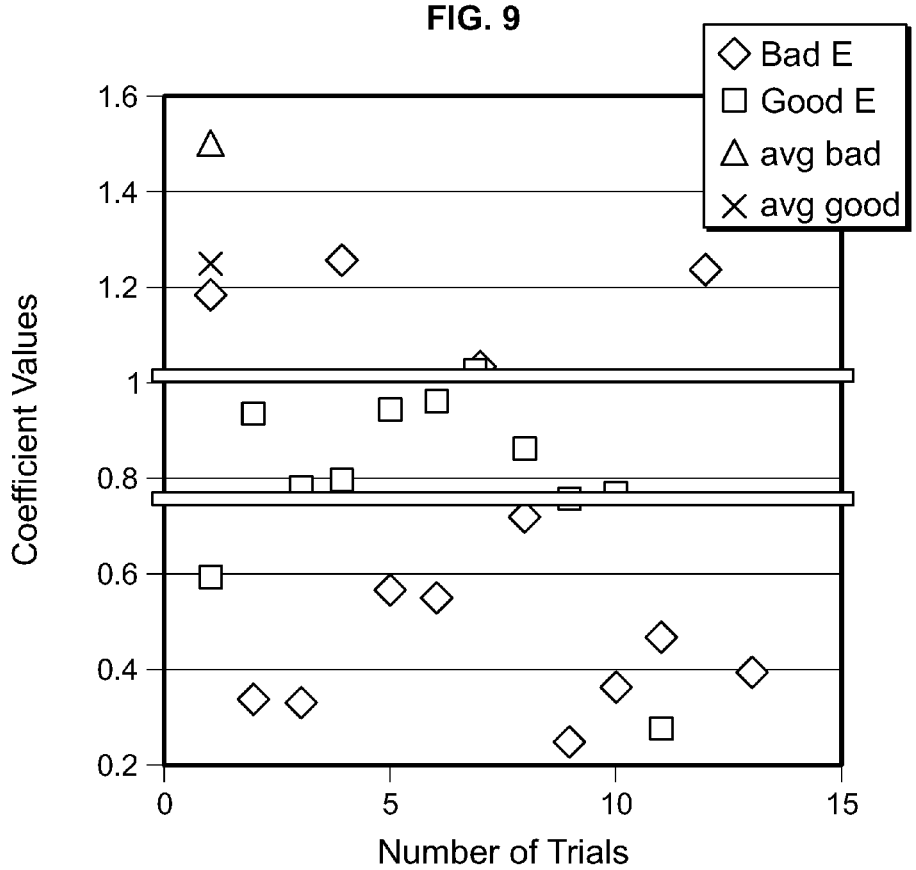
FIG. 10 is a graph comparing a dominant coefficient of the intensity curve fit function to that of the template curve of the nominal deposition.

To fit the entire time history of pin operations, two ADS functions may be used: one for Phases I and II and the second ADS for Phases III and IV. By examining the distribution pattern of the coefficients, defective spots can be detected. Depending on the particular mathematical function chosen, one or more parameters may be more sensitive to spot anomalies. An example of distribution separation is shown in FIG. 10 where coefficient "e" of the double sigmoidal function is analyzed. From the database, it is determined a priori that a distribution from 0.78 to 1 for coefficient "e" results in normal spots. For a particular dispensation, if coefficient "e" falls outside this range, the corresponding spot may be defective. Analysis of the combination of all of the coefficients further improves the classification accuracy and ultimately to determine whether a droplet is defective.

Figure 11:
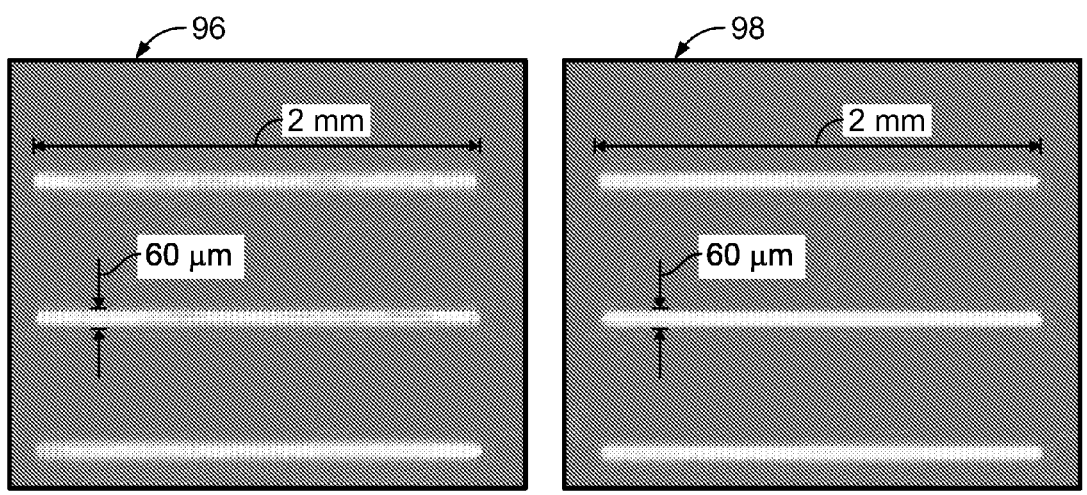
FIG. 11 illustrates scanned images of lines drawn using a spot-sequence method and a liquid-column sweeping method.

In another aspect of the present invention, the liquid delivery system 10 can be used to generate lines of liquid material using two different methods. FIG. 11 shows the scanned images of lines drawn using a spot-sequence method 96 and a liquid-column-sweeping method 98. The spot-sequence method 96 involves generating a series of spots (droplets) with minimal spacing between adjacent spots to form a line.

The liquid-column-sweeping method 98 involves using the liquid column 74 (see FIG. 4D) formed during elongation. More particularly, after the liquid column 74 is formed as the liquid delivery apparatus 14 is being moved in the upward direction away from the target surface 40, vertical movement of the liquid delivery apparatus 14 ceases and the liquid delivery apparatus 14 is moved horizontally along the target surface 40 while liquid is continuously dispensed. Because the internal force of the liquid column 74 overcomes the adhesive force between the liquid and the target surface 40, a line can be drawn along the target surface 40 without interrupting the geometry of the liquid column 74. The liquid-column-sweeping method requires real-time control of the footprint of the liquid column 74 to maintain a constant line width. Due to manufacturing tolerances, the target surface 40 includes micro-projections and micro-crates which create irregularities on the target surface 40. Because the light intensity measured by the photo sensor 24 is affected by the footprint of the liquid column 74, real-time measurement of the light intensity can be used to generate line drawings, and compensations for micro-projections and micro-crates can be made by moving the liquid delivery apparatus 14 up or down with respect to the substrate.

One particular application of the liquid delivery system 10 is DNA/protein microarray fabrication. Considering that the liquid delivery system 10 can be used to generate lines, the liquid delivery system 10 can be used for other applications, such as semiconductor, micro-electro mechanical systems, and nanosystems. For example, the liquid delivery system 10 can be used to produce transistors and single wall carbon nanotubes.

It will be understood that the embodiments described herein are merely exemplary and that a person skilled in the art may make many variations and modifications without departing from the spirit and scope of the invention. All such variations and modifications are intended to be included within the scope of the invention as defined by the appended claims.

What is claimed is:

1. A method of dispensing a liquid material, comprising the steps of:
   (a) moving a liquid delivery apparatus having liquid material contained in a cavity toward a predetermined location until a droplet of liquid material formed on a tip of the liquid delivery apparatus contacts the predetermined location;
   (b) providing light from a light source directed at the liquid material and measuring the intensity of light during step (a);
   (c) monitoring step (a) in real-time based on the measured light intensity;
   (d) moving the liquid delivery apparatus away from the predetermined location such that the liquid material elongates and moving the liquid delivery apparatus horizontally along a predetermined area after the liquid material elongates, while the liquid material is continuously dispensed, to generate a line of liquid material;
   (e) measuring the intensity of light during step (d); and
   (f) monitoring step (d) in real-time based on the measured light intensity from step (e).

2. The method of claim 1, further comprising the step of continue moving the liquid delivery apparatus away from the predetermined location such that the liquid material pinches off.

3. The method of claim 2, further comprising the step of measuring the intensity of light during the steps of moving the liquid delivery apparatus away from the predetermined location such that the liquid material elongates, and continue moving the liquid delivery apparatus away from the predetermined location such that the liquid material pinches off.

4. The method of claim 3, wherein the liquid material remains on the liquid delivery apparatus until the liquid material pinches off.

5. The method of claim 4, wherein the droplet of liquid material is formed on a tip of the liquid delivery apparatus by moving a pin toward the predetermined location.

6. The method of claim 4, wherein the droplet of liquid material is formed on a tip of the liquid delivery apparatus by moving a plunger toward the predetermined location.

7. The method of claim 4, wherein the step of monitoring includes the steps of:
   deriving a profile for a reference curve to determine the light intensity expected during a processing cycle, where the processing cycle includes the steps of (a) moving a liquid delivery apparatus having liquid material contained in a cavity toward a predetermined location until a droplet of liquid material formed on a tip of the liquid delivery apparatus contacts the predetermined location, (b) moving the liquid delivery apparatus away from the predetermined location such that the liquid material elongates, and (c) continue moving the liquid delivery apparatus away from the predetermined location such that the liquid material pinches off;
   providing light from a light source directed at the liquid material; and
   comparing the intensity of light measured during the processing cycle against the profile of the reference curve while performing the processing cycle.

8. The method of claim 7, wherein deriving a profile for a reference curve comprises executing test process cycles to determine the average light intensity for each step of the processing cycle.

9. The method of claim 4, wherein the step of monitoring includes the step of curve fitting the measured light intensity with asymmetric double sigmoidal.

* * * * *

UNITED STATES PATENT AND TRADEMARK OFFICE
CERTIFICATE OF CORRECTION

| | | |
|---|---|---|
| PATENT NO. | : 8,227,258 B2 | Page 1 of 1 |
| APPLICATION NO. | : 12/369295 | |
| DATED | : July 24, 2012 | |
| INVENTOR(S) | : Timothy Chang et al. | |

It is certified that error appears in the above-identified patent and that said Letters Patent is hereby corrected as shown below:

In the Claims:

Claim 5, column 8, line 28, "a" should be --the--; and

Claim 6, column 8, line 31, "a" should be --the--.

Signed and Sealed this
Thirteenth Day of November, 2012

David J. Kappos
*Director of the United States Patent and Trademark Office*